United States Patent [19]

Jass

[11] 4,149,250
[45] Apr. 10, 1979

[54] METHOD AND APPARATUS FOR PRODUCING A CROSS SECTIONAL IMAGE OF A BODY

[75] Inventor: Wieland Jass, Munich, Fed. Rep. of Germany

[73] Assignee: Siemens Aktiengesellschaft, Munich, Fed. Rep. of Germany

[21] Appl. No.: 715,507

[22] Filed: Aug. 18, 1976

[30] Foreign Application Priority Data

Aug. 21, 1975 [DE] Fed. Rep. of Germany ....... 2537333

[51] Int. Cl.² .......................... G01T 1/16; G06F 15/42
[52] U.S. Cl. .................................. 364/414; 250/445 T
[58] Field of Search .................. 235/151.3; 250/445 T, 250/366; 358/111; 364/414, 527

[56] References Cited

U.S. PATENT DOCUMENTS

| | | |
|---|---|---|
| 3,778,614 | 12/1973 | Hounsfield .................. 250/445 T X |
| 3,867,634 | 2/1975 | Hounsfield .................. 250/445 T X |
| 3,894,181 | 7/1975 | Mistretta et al. ................ 358/111 X |
| 3,924,129 | 12/1975 | LeMay .......................... 250/445 T X |
| 3,944,833 | 3/1976 | Hounsfield .................. 250/445 T X |
| 4,029,948 | 6/1977 | Radiography .................. 358/111 X |

*Primary Examiner*—Edward J. Wise
*Attorney, Agent, or Firm*—Kenyon & Kenyon, Reilly, Carr & Chapin

[57] ABSTRACT

An improved method and apparatus for producing a cross sectional image of a body using a method where the distribution of the attenuation coefficients of ionizing rays passing through the body in a cross sectional plane is derived using a convolution method, in which a plurality of convolution kernels are permanently stored for use as desired and measured data obtained and convoluted therewith after which values are added and displayed on a display device permitting different settings of image contrast to thereby harmonize the cross sectional image of the body.

5 Claims, 13 Drawing Figures

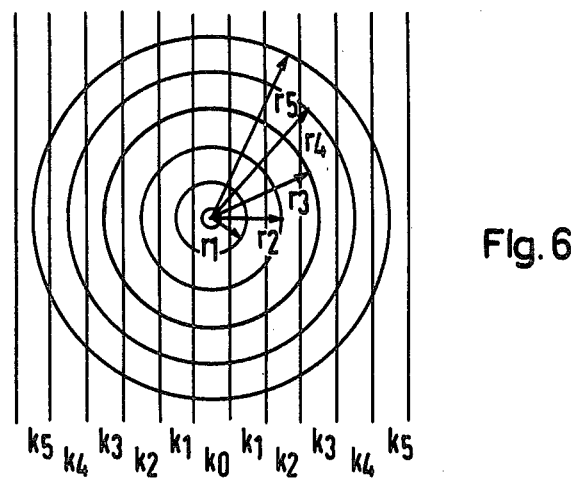
Fig. 6
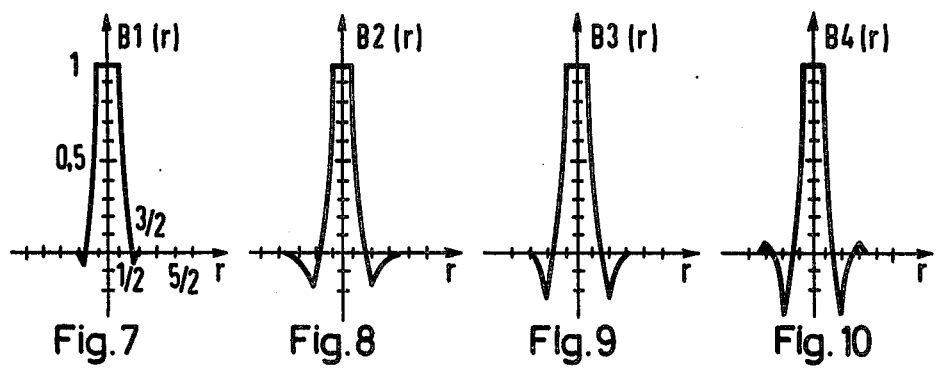
Fig. 7  Fig. 8  Fig. 9  Fig. 10
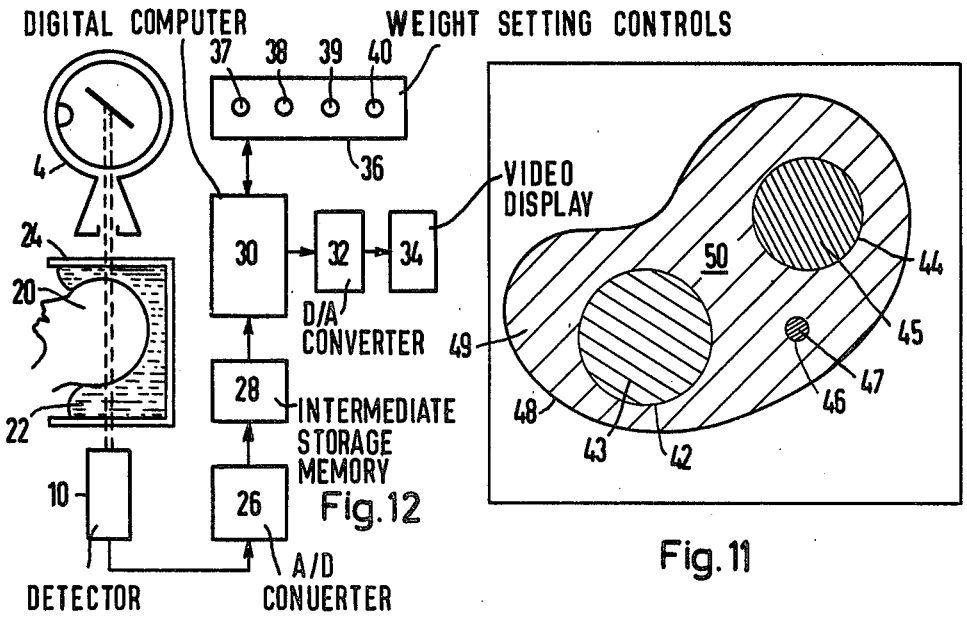
Fig. 12
Fig. 11

METHOD AND APPARATUS FOR PRODUCING A CROSS SECTIONAL IMAGE OF A BODY

BACKGROUND OF THE INVENTION

This invention relates to the production of cross sectional images of a body from measurements made using ionizing rays in general and more particularly to an improved method and apparatus for providing improved contrast in images generated in this manner.

Scanners have recently been developed by means of which a body may be scanned by moving a radiation source and radiation receiver parallel to the cross sectional plane of the body. In some models parallel displacement of the radiation source and the radiation receiver becomes unnecessary, when a fanshaped beam of rays with a multiplicity of radiation receivers is used. The heavily focused rays pass through the body in a cross sectional plane in such a manner that at least some rays always intersect in an image element. In known methods, the distribution of the attenuation coefficients in the cross sectional plane of the body can be derived by a convolution method through correction of measured data. In such a method the measurement data is convolved with a convolution kernel whereafter additive superposition of the convolved measurement data is carried out and reprojection of the image then accomplished. The measured values are converted into electrical signals and evaluated in an electronic computing system.

In one known method for producing a cross section image of the body, an X-ray or gamma-ray source furnishes a beam of nearly parallel rays which penetrates the body to be examined in the cross section plane and is absorbed by the body to a certain extent. Behind the body to be examined, the radiation falls on a detector. By displacing the radiation source and the detector parallel, step by step, the body is scanned sequentially in the cross section plane. Thereupon, the radiation source and the detector are tilted at a predetermined angle to an axis perpendicular to the cross section plane and the cross section plane of the body is again projected on the detector by parallel displacement. The radiation therefore passes through the individual image elements in a different direction. If this process is repeated several times, each element of the body in the cross section plane is imaged as many times as the system is tilted about the axis at a predetermined angle. The conversion of these different individual exposures of the cross section image to be produced of the body is obtained by means of an electronic computer, into which then, for instance, 28,000 equations with 6,400 variables are set. The cross section is first calculated by the electronic computer as a two-dimensional field of numbers, and subsequently, the numerical values of the individual image elements can be converted and displayed as a picture which is easy to interpret or can also be printed out by a printer (German Offenlegungschrift No. 1,941,433).

In this known method, the numerical reconstruction is arranged so that the pictures produced faithfully resemble the original cross section image, i.e. the numerical values in the individual image elements represent, with the exception of measurement or equipment errors, the unchanged radiation attenuation coefficients in the cross section plane of the object, averaged over a small area.

If the direction of radiation is fixed, the radiation source and the receiver go successively through discrete positions to scan the object in the cross section plane with a set of parallel-ray beams. The direction of radiation is varied through a range of 180° in individual angular steps of say 1°. The measured values of the radiation attenuations of a single measurement series determined by parallel displacement are subsequently corrected point by point. After this correction, each measured value represents the sum of the radiation attenuation coefficients over the strip region covered by the measuring beam. In the second step, the corrected individual measurement series is convolved with a predetermined, permanently stored convolution kernal. In the third step, an intermediate image is produced from the convolved measurement series by re-projection. In the re-projection, every value of the series is uniformly distributed in the image plane over the strip region which is assigned to it according to the ray penetration geometry. In the last step, all intermediate images belonging to all radiation directions are summed by simple superposition to form the cross section image of the body (IEEE Transactions on Nuclear Science, June 1974, Vol. NS-21 no. 3 pages 46–49 and pages 59–63).

With this known method, cross sectional images of a body with numerical values in the individual image elements true to the original, except for measurement and method errors are also obtained. In practice, however, not only are such faithfully reproduced cross section images desired, but constrasting filtered cross sectional images are also desireable.

SUMMARY OF THE INVENTION

It is therefore an object of the invention to provide a method and apparatus for producing cross section images of the body, which permit the character of the contrast of the cross section image can be varied at will.

It is well known that in X-ray television equipment, an additional device can be provided between the television camera scanning the picture on the fluorescent screen and the picture reproducing equipment, for enhancing the contrast of small picture details by suppressing the large area zones of the picture. The picture on the fluorescent screen can be scanned, for instance, by means of two television cameras, the video signal trains of which are fed to a subtractive mixer. By means of the difference signal produced thereby, which now still contains only the essential details, the picture-reproducing tube is modulated in a manner known per se. It is also possible to divide the video signal train generated by the television camera over separate channels and to cover the signal train of the one channel with an auxiliary display set which is scanned by an auxiliary television camera. The apparatus may further be designed as a video highpass filter for "harmonizing" and be equipped with an image pickup tube of the charge storage type. In these known devices, the character of the contrast of the X-ray picture is afterwards changed, and substantial additional equipment is required for this purpose (German Offenlegungsschrift No. 1,224,352).

According to the present invention, the stated object is achieved by permanently storing several convolution kernels for use as desired. Symmetrical discrete functions are chosen as convolution kernels. In one particular embodiment of the method, the convolution kernels can also be superimposed additively. By selecting the individual convolution kernels, and preferably a whole series of convolution kernels, the character of the contrast of the cross section image of the body produced can be changed at will. It is a particular advantage of the method that not only the contour sharpness of the individual areas of the body cross section image, but in addition, the brightness differences between these individual areas, can be varied.

With the method according to the present invention, an entire series of one dimensional convolution kernels is permanently stored ready for use when called up. The kernels in this series are chosen so that cross section images which are differentiated to an increasing degree are obtained. If these kernels are used, resulting image pulse functions are obtained which become different.

BRIEF DESCRIPTION OF THE DRAWINGS

FIG. 6 is a graph illustrating how a resulting image pulse function is brought about from a convolution kernel.

FIGS. 7 to 11 illustrate the effect of the convolution kernels on the picture contrast by means of the corresponding resulting image pulse functions.

FIG. 12 is a schematic block diagram of apparatus for implementing the method according to the present invention.

DETAILED DESCRIPTION OF THE INVENTIONS

Figure 1:
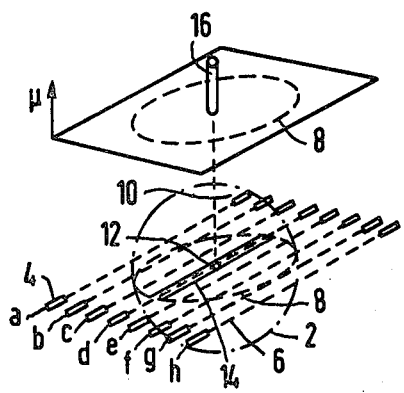
FIGS. 1 to 5 are graphical illustrations of the individual procedure steps of the present invention.

According to FIG. 1, there is arranged on one side of a body 2, the contour of which is indicated by the dash-dotted line, a radiation source 4, the ray bundle 6 of which penetrates the body 2 in a plane which is to be displayed as a body cross section and the boundary line of which is designated in the figure with 8. The ray bundle 6 penetrates the body 2, in the body cross section plane, is partially absorbed there and then strikes a detector 10, which furnishes a measured value of the incident radiation. This measured value is converted into an electrical signal by cnventional electronics not shown in the figure. Through parallel displacement of the radiation source 4 and the receiver 10 from the position a in successive steps via the positions b, c, d, e, f, g up to the position h, a series of measurement values which yield the attenuation values of the parallel rays in the cross section plane of the body is obtained.

In FIG. 1, the radiation penetration situation for an individual, singled out body element 12 is shown. In the upper part of the figure, the image pulse function 16 belonging to the body element 12 is shown, the height of which indicates the magnitude of the absorption coefficient $\mu$ in the body element 12.

To determine the distribution of the radiation attentuation coefficient $\mu$ in the body cross section plane, the attenuation values f(i) of the radiation for the individual positions a, b, c, ... h are first measured in the measuring apparatus and, if necessary, corrected in accordance with the radiation used. An attenuation of the intensity will occur in the position d of the measuring apparatus along the body part 14 which is penetrated by the ray. Subsequently, a convolution kernel K is applied to the series f(i) of the measured values, which results in a convolved measurement series $f_K(j)$. The values of the convolved measurement series are distributed over the image area along parallel strips which correspond to the body parts irradiated during the measurement, and furnish an intermediate image. Each value of the convolved measurement series is distributed as a constant over the corresponding strip. In the last step, the body cross section image is obtained by additive superposition of all the intermediate images corresponding to the different measuring directions.

Figure 2:
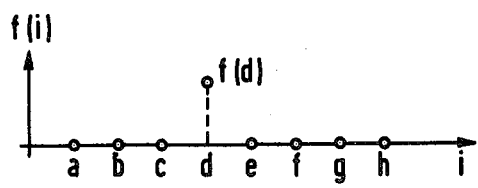
Figure 3:
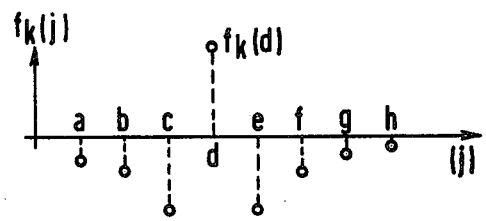

In the diagram of FIG. 2, the index i of the beam positions a to h of the radiation source 4 and the radiation receiver 10 is plotted along the abscissa and the corresponding corrected measurement values f(i) along the ordinate. In the position d, the radiation intensity f(d) appears as the measurement value. The values of the corrected individual measurement series convolved with a convolution kernel K follow the shape of the function $$f_K(j) = \sum_{i=1}^{n} K(j-i) \cdot f(i),$$

where i and j are integers from 1 to n and k(l) is a kernel of the series provided. The kernels in the provided series are symmetrical discrete functions, i.e., K(l)=K(l). As the result of the convolution with the kernel K for a singled out measurement value f(d), the convolution kernel shifted with its center to the position d and multiplied by the measured value f(d) is obtained from the diagram of FIG. 3.

A numerical example for a series of 4 one dimensional convolution kernels follows:

(a) $K1(0) = 1, K1(\pm l) = -\dfrac{1}{(2l-1)(2l+1)}$,
$l = 1, 2, 3, \ldots$ (b) $K2(0) = 1, K2(\pm 1) = -1/2, K2(\pm l) = 0$,
$l = 2, 3, 4, \ldots$ (c) $K3(0) = 1, K3(\pm 1) = -\dfrac{1}{2 - (2/3)^3}$, $K3(\pm l) = Q \cdot \left[ \dfrac{1}{(2l-1)^3} - \dfrac{1}{(2l+1)^3} \right]$, $l = 2, 3, 4, \ldots$ with $Q = \dfrac{4}{2 - (2/3)^3}$, (d) $K4(0) = 1, K4(\pm 1) = -2/3, K4(\pm 2) = 1/6$,
$K4(\pm l) = 0, l = 3, 4, 5, \ldots$ where K1 is the convolution kernel of the known method. In principle, the kernels $K_1$ and $K_3$ have infinitely many values different from zero, while the kernels $K_2$ and $K_4$ are different from 0 only at 3 or 5 points. In some cases it may be advantageous to use only a single one of these permanently stored kernels for the convolving operation. If, for instance, only one of the kernels $K_2$ and $K_4$ is used, then the convolving effort is also reduced substantially over a convolving operation with the kernel $K_1$. If several kernels are used, a substantial reduction of the convolving effort is therefore possible as compared to the convolving method with the kernel $K_1$.

Figure 5:
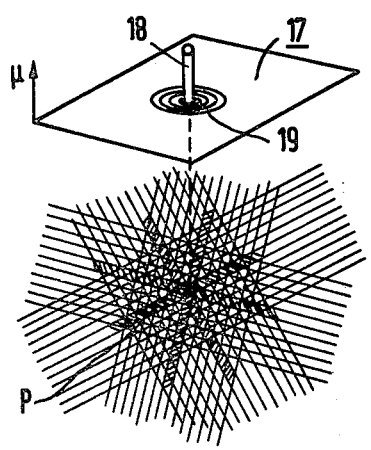
Figure 4:
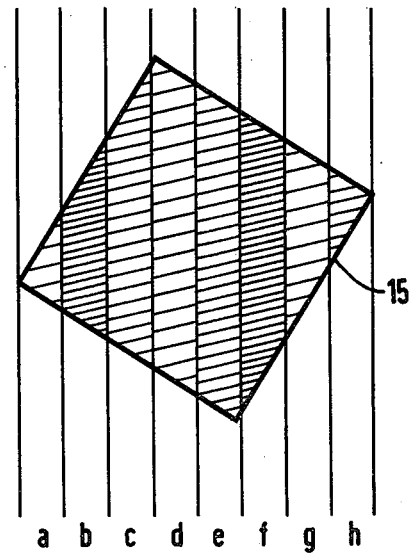

By re-projecting the convolved measurement series $f_K(j)$ over the image area, one obtains a strip image 15, the different radiation attenuations of which are indicated in FIG. 4 by different shading of the strips. By superimposing all strip images of the different directions, of which only four are indicated in FIG. 5, one obtains the attenuation coefficient $\mu$ in the image element 12. Through the use of the further stored convolution kernels $K_2$ to $K_4$, negative values for the rotationally symmetric spreading of the resulting image pulse function 17 of the image element 12 are obtained. This resulting image pulse function consists of a central pulse 18 and a rotationally symmetric function component which is indicated in the figure by concentric circles 19. The negative values cause a differentiation of the cross section image and therefore lead to a change of the character of the contrast.

In the example shown of an individual, singled out body element 12 according to FIGS. 1 to 5, the resulting image pulse function specifically belonging to the image element 12 and the convolution kernel K is obtained.

The interrelation between a single convolution kernel K and the resulting image pulse function B(r) of the body cross section image to be produced is shown in FIG. 6 in conjunction with FIGS. 7 to 10. Through re-projection from the kernel K, a strip picture as shown on FIG. 6 is produced with the numerical values in the individual strips $K(\pm l)=kl$, $l=0, 1, 2, 3, ...$ of the symmetrical convolution kernel. A good approximation of the resulting image pulse function B(r) is obtained from the path integrals, divided by r, of the strip image function along the concentric circles, the radii of which are designated in the figure as $r_1$ to $r_5$. The smallest circular integration path with the radius $r_0$ is not designated in the figure.

The shape of the resulting image pulse function B1(r) for the kernel K1 is shown in FIG. 7. Note the small negative component of the function for the convolution kernel K1. This negative component increases in the resulting image pulse function B2(r) of the convolution kernel K2 shown on FIG. 8 and further in the resulting image pulse function B3(r) and B4(r) as shown on FIGS. 9 and 10 with convolution kernels $K_3$ and $K_4$, respectively. This increasing negative component causes an increasing differentiation and thereby, the respective character of the contrast of the cross section image.

FIG. 11 illustrates how the contours 42, 44, 46 and 48 of different picture areas 43, 45, 47 and 49 in a body cross section 50 as well as the brightness differences between the individual picture areas can be set at will. The brightness differences are indicated in the figure by different shading.

FIG. 12 illustrates apparatus for carrying out this method. In this figure, elements identical to those of FIG. 1 are given the same reference numerals. As illustrated, a person's head 20 is surrounded by a water filled cap 22 arranged in a housing 24 to prevent the head from shifting during a multiplicity of measuring operations. The radiation after being attenuated when passing through the head 20 is received by a detector 10 where it is converted into an analog electrical signal in conventional fashion. The analog signal is converted in an analog to digital converter 26 into a digital signal. A type of converter which may be used is then known as the "Analogic" manufactured by the Wakefield Company. The converted data is stored in an intermediate storage memory 28 which may be, for example, a disc recorder such as those manufactured by Digital Equipment Corporation. Data is stored throughout the scanning operation. This is raw attenuation data obtained by such scanning. The data so obtained is supplied to a digital computer 30. A typical computer which can be used for this purpose is a PDP 11 also made by the Digital Equipment Corporation. Using known processing techniques, the computer calculates from the attenuation measurements an attenuation coefficient matrix which corresponds to the layer examined. This can be printed out directly using an electronic printer if desired. However, a numerical picture of this nature is relatively hard to evaluate. Thus, it is more advantageous to convert this numerical information, into a picture representing the cross sectional image. Thus, there is shown a digital to analog converter 32 which converts this numerical data into analog values which may then be used in a conventional video display 34 to display such a picture. A display of the type which can store the data supply to it so as continue to display the image as long as desired is preferably used. The display may then be photographed if desired.

The apparatus thus far described is conventional. In accordance with the present invention, there is provided an addition to this apparatus a device 36 which permits selecting as the convolution kernel to be used in obtaining the corrected individual measurement series illustrated by FIG. 2, any desired linear combination of the permanently stored series of kernels. Thus, this permits setting up the following:

$$k(1)=c_1\cdot K1(1)+c_2\cdot K2(1)+c_3\cdot K3(1)+c_4\cdot K4(1),$$

where $c_1$ to $c_4$ are selectable constants and K1 to K4 are the stored convolution kernels. The weighting parameters $c_i$ are set by corresponding selector knobs 37 to 40 which may be, for example, digital shaft encoders. These settings are provided as inputs to the digital computer 30 which then uses this data in determining the convolution kernels to be used in processing the measurement data.

With a convolution kernel set in this manner, a resulting image pulse function is obtained which is a linear combination of the resulting image pulse functions B1 to B4 associated with the kernels K1 to K4 with the same weighting parameter $c_i$, i.e. for the example given:

$$B(r)=c_1\cdot B1(r)+c_w\cdot B2(r)+c_3\cdot B3(r)+c_4\cdot B4(r).$$

This is a direct result of the fact that the numerical cross sectional image reconstruction method of the present invention has a property of an undisturbed superposition with respect to the convolution kernels of the corrected individual measurement series. Through the free choice of the weighting parameters $c_i$ it is therefore possible not only to set a number of basic kinds of constrasts but also to mix them at will.

Figure 13:
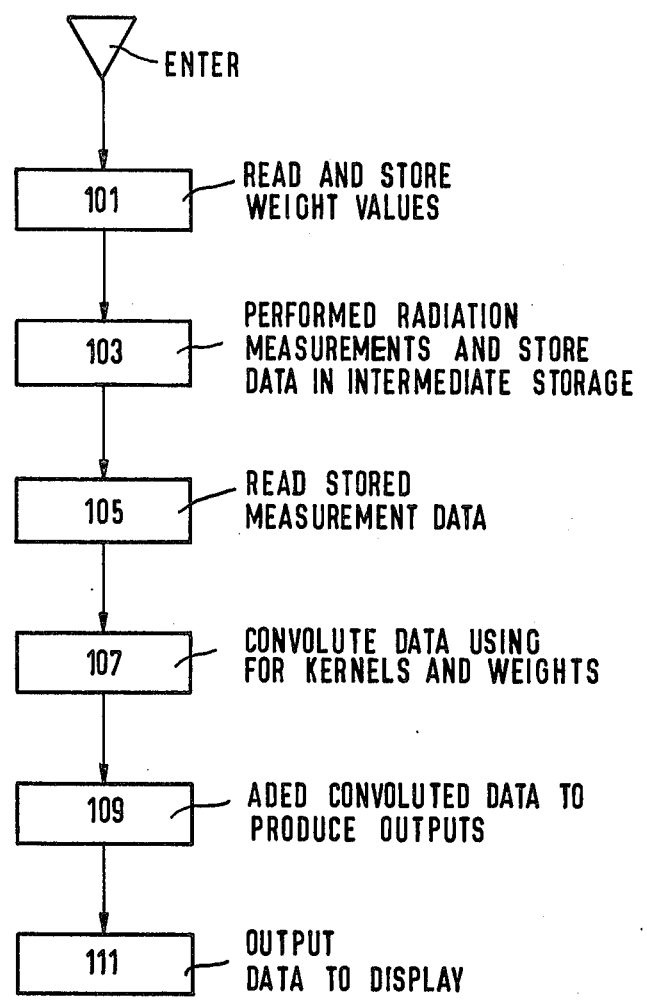
FIG. 13 is a basic flow chart for said apparatus as illustated by FIG. 12.

The basic flow chart for the digital computer 30 is illustrated on FIG. 13. The operator selects the types of contrast he desires by setting up the weight setting controls 37–40 in the device 36. As indicated on FIG. 13, the digital computer is programmed, as indicated by block 101 to read and store these weight values. The radiation measurements are then performed and the measurement data stored in the intermediate storage memory 28 as indicated by block 103. Thereafter, the digital computer 30 is caused to read the stored measurement data as indicated by block 105. Then, using the weights set and the pre-stored convolution kernels the data is convolved as indicated by block 107 whereafter, as indicated by block 109 the convolved data is added to produce the desired output values which are then output to the digital to analog converter for display purposes as indicated at block 111.

It is also possible to associate a number of convolution kernels having a predetermined mixing ratio with a single control knob. For example, instead of using four control knobs as illustrated by FIG. 12, one knob can be used for setting a desired sharpness of the contours 42, 44, 46 and 48 of different picture areas 43, 45, 47 and 49 as illustrated on FIG. 11. In such a case, a further knob can be provided for setting the brightness differences between adjacent picture areas 43 or 45 or 47 or 49 and a further knob for setting the brightness differences between the adjacent picture areas, e.g. the picture areas 43, 45, 47 and background 49 of the cross sectional image 50.

Although in the example given in FIG. 12, a portion of a human body is chosen as the body of which the cross sectional image is taken, it is possible with the method of the present invention to examine cross sectional images of other objects. Thus, the present invention is also suitable for non-destructive material testing.

I claim:

1. In a method for producing a cross sectional image of a body from the distribution of measured total absorption values of ionized rays which penetrate the body in the cross sectional plane and of which at least some rays intersect elements of the image, in which method the distribution of the attenuation coefficients in the body cross sectional plane is derived by a convolution method including the steps of:
   (a) correcting the measured values obtained by passing radiation through the body to take into account particular radiation in use to obtain a corrected measurement series;
   (b) convolving the corrected measurement series using a stored convolution kernel; and
   (c) re-projecting and additively superimposing the convolved measurement series, the improvement comprising the steps of;
   (d) permanently storing a plurality of convolution kernels; and
   (e) forming the convolution kernel to be used in the step of convolving by multiplying each of a plurality of the stored convolution kernels by a preselected constant and then performing an additive superimposition of the multiplication results.

2. The method according to claim 1 wherein different multiplication factors are used for adjusting the contour sharpness and for adjusting the brightness differences of the body cross section image in each case.

3. In apparatus for producing a cross sectional image of the body from a distribution of measured total absorption values of ionized rays which penetrate the body in the cross sectional plane and of which at least some rays intersect elements of the image, said apparatus including:
   (a) means for generating ionized rays;
   (b) means for detecting said ionized rays after passing through a body to be measured providing an analog output;
   (c) means for causing said generating and detecting means to be scanned across the sectional plane to be measured;
   (d) means to convert the analog detected values into digital values;
   (e) means to store the measured digital values;
   (f) computing means for
      1. storing a convolution kernel;
      2. correcting the measured values to take into account the radiation in use;
      3. convolving the measurement series with the stored convolution kernel; and
      4. re-projecting and additively superimposing the convolved measurement series; and
   (g) means for displaying the data so obtained, the improvement comprising:
   (h) means for storing a plurality of separate convolution kernels, and weighting parameters; and
   (i) means for setting and supplying to said digital computer, for storage in said means for storing, a weighting parameter by which each of said kernels is to be multiplied, said computing means adapted to form the convolution kernel to be used with said measurement series by additively superimposing said plurality of stored convolution kernels multiplied by their associated weighting parameters.

4. Apparatus according to claim 3 wherein means for setting are associated with each of said convolution kernels.

5. Apparatus according to claim 3 wherein said means for setting weighting parameters comprise means for generating weighting parameters which control the contour sharpness and the brightness differences in the body cross section image.

* * * * *